(12) United States Patent
Brutinel et al.

(10) Patent No.: US 10,344,253 B2
(45) Date of Patent: Jul. 9, 2019

(54) DEVICES AND KITS FOR THE PROPAGATION OR STORAGE OF MICROORGANISMS, AND METHODS OF MAKING AND USING

(71) Applicant: 3M INNOVATIVE PROPERTIES COMPANY, St. Paul, MN (US)

(72) Inventors: Evan D. Brutinel, Inver Grove Heights, MN (US); Alexi J. Young, Shoreview, MN (US); Adam J. Stanenas, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/519,944

(22) PCT Filed: Nov. 16, 2015

(86) PCT No.: PCT/US2015/060834
§ 371 (c)(1),
(2) Date: Apr. 18, 2017

(87) PCT Pub. No.: WO2016/085688
PCT Pub. Date: Jun. 2, 2016

(65) Prior Publication Data
US 2017/0355943 A1 Dec. 14, 2017

Related U.S. Application Data

(60) Provisional application No. 62/084,070, filed on Nov. 25, 2014.

(51) Int. Cl.
| | |
|---|---|
| C12M 1/12 | (2006.01) |
| C12M 1/00 | (2006.01) |
| C12M 1/34 | (2006.01) |
| C12Q 1/04 | (2006.01) |
| A61L 2/08 | (2006.01) |
| C12Q 1/06 | (2006.01) |

(52) U.S. Cl.
CPC ............ *C12M 23/04* (2013.01); *A61L 2/081* (2013.01); *A61L 2/087* (2013.01); *C12M 23/20* (2013.01); *C12M 25/06* (2013.01); *C12M 41/36* (2013.01); *C12M 45/22* (2013.01); *C12Q 1/04* (2013.01); *C12Q 1/06* (2013.01)

(58) Field of Classification Search
CPC ..................................................... C12M 23/04
See application file for complete search history.

(56) References Cited

U.S. PATENT DOCUMENTS

| | | | |
|---|---|---|---|
| 1,520,217 A | 8/1924 | Auperl | |
| 3,935,067 A | 1/1976 | Thayer | |
| 3,935,076 A | 1/1976 | Cymbalisty | |
| 4,565,783 A | 1/1986 | Hansen | |
| 5,089,413 A | 2/1992 | Nelson | |
| 5,232,838 A | 8/1993 | Nelson | |
| 5,364,766 A | 11/1994 | Mach | |
| 5,409,838 A | 4/1995 | Wickert | |
| 5,443,963 A | 8/1995 | Lund | |
| 5,462,860 A | 10/1995 | Mach | |
| 5,601,998 A | 2/1997 | Mach | |
| 5,635,367 A | 6/1997 | Lund | |
| 5,681,712 A | 10/1997 | Nelson | |
| 7,153,696 B2 * | 12/2006 | Fukuoka | C12Q 1/28 436/164 |
| 7,371,464 B2 | 5/2008 | Sherman | |
| 7,695,818 B2 | 4/2010 | Sherman | |
| 8,846,335 B2 | 9/2014 | Moeller | |

FOREIGN PATENT DOCUMENTS

| | | |
|---|---|---|
| CA | 2107350 | 10/1992 |
| CN | 1550771 | 12/2004 |
| CN | 101096634 | 1/2008 |
| CN | 102131915 | 7/2011 |
| CN | 102459565 | 5/2012 |
| EP | 1 473 563 | 11/2004 |
| GB | 1520217 | 8/1978 |
| JP | 2002-171963 | 6/2002 |
| JP | 2005-109729 | 4/2005 |

(Continued)

OTHER PUBLICATIONS

Thomas et al. American J of Epidemiology, 1979, 110(4):515-521.*
Simpson, Geotextiles and Geomembranes, 1991, 10:187-191.*
Buzoleva, LS. [Use of bentonite clays as accumulation media for enterobacteria]. Primenenie bentonitivykh glin v kachestve sred nakopleniia dlia enterobakterii. Klinicheskaia laboratomaia diagnostika, Jun. 2001, No. 6, pp. 47-50.
Valle, "SarA and not sigmaB is essential for biofilm development by *Staphylococcus aureus*", Mol Microbiol., 2003, vol. 48, No. 4, pp. 1075-1087.
International search report for PCT International Application No. PCT/US2015/060834 dated Mar. 4, 2016, 5 pages.

*Primary Examiner* — Bin Shen
(74) *Attorney, Agent, or Firm* — Adrian L. Pishko (57) ABSTRACT

Devices for the propagation or storage of microorganisms are provided including a first layer that has a first portion of a surface of the first layer, to which a first water-swellable gelling agent comprising a first clay is affixed. The devices further include a second layer that is separable from the first layer and has a first portion of a surface of the second layer, to which a second water-swellable gelling agent is affixed. Methods for detecting and enumerating at least one microorganism in a sample are provided. The methods include providing a device, separating the first layer from the second layer, adding an aliquot of a sample containing at least one microorganism onto the first or second water-swellable gelling agent to form an inoculated device, laminating the first layer back to the second layer, and incubating the inoculated device. Kits and methods of making the devices are also provided.

17 Claims, 5 Drawing Sheets

(56) References Cited

FOREIGN PATENT DOCUMENTS

| | | |
|---|---|---|
| JP | 2005-113080 | 4/2005 |
| JP | 2005-295887 | 10/2005 |
| JP | 2006-288217 | 10/2006 |
| WO | WO 82/02563 | 8/1982 |
| WO | WO 1982-02563 | 8/1982 |
| WO | WO 1996-15715 | 5/1996 |
| WO | WO 2010/022111 | 2/2010 |
| WO | WO 2010/141326 | 12/2010 |
| WO | WO 2012-012104 | 1/2012 |
| WO | WO 2013-143508 | 10/2013 |
| WO | WO 2015-134686 | 9/2015 |

* cited by examiner

DEVICES AND KITS FOR THE PROPAGATION OR STORAGE OF MICROORGANISMS, AND METHODS OF MAKING AND USING

CROSS REFERENCE TO RELATED APPLICATIONS

This application is a national stage filing under 35 U.S.C. 371 of PCT/US2015/060834, filed Nov. 16, 2015, which claims the benefit of U.S. application Ser. No. 62/084070, filed Nov. 25, 2014, the disclosure of which is incorporated by reference in its/their entirety herein.

FIELD

The disclosure relates to devices useful for the growing and detection of microorganisms, including water-swellable gelling agents. This disclosure also relates to methods of making the devices, kits, and methods of propagating or storing microorganisms using the devices.

BACKGROUND

Dehydrated microbial culture devices are known which rely on guar and other natural gums as cold soluble gelling agents. Natural gums work well in most applications and have superior gelling characteristics compared to other cold soluble polymers. Disadvantages of the use of natural gums include that some organisms are able to metabolize the natural gum's sugar chains, resulting in at least some liquefaction of the plate. Further, natural gums tend to break down under levels of ionizing radiation typically used to decontaminate or sterilize a plate.

Hence, there remains a need for devices for propagation or storage of microorganisms that provide features such as increased resistance to organism metabolism, ionizing radiation, etc.

SUMMARY

Devices and methods for the propagation or storage of microorganisms are provided. In a first aspect, a device is provided. More particularly, a device is provided including a first layer that has a first portion of a surface of the first layer, to which a first water-swellable gelling agent comprising a first clay is affixed. The device further includes a second layer that is separable from the first layer and has a first portion of a surface of the second layer, to which a second water-swellable gelling agent is affixed.

In a second aspect, a method of making a device is provided. The method includes providing a first layer having a surface; affixing a first water-swellable gelling agent including a first clay to a first portion of the surface of the first layer; providing a second layer having a surface; and affixing a second water-swellable gelling agent to a first portion of the surface of the second layer. The method further includes laminating the first layer to the second layer, in which the first water-swellable gelling agent at least partially contacts the second water-swellable gelling agent. Optionally, the device is decontaminated or sterilized using ionizing radiation.

In a third aspect, a method of detecting and enumerating at least one microorganism in a sample is provided. The method includes providing a device according to the first aspect, separating the first layer from the second layer, adding an aliquot of a sample containing at least one microorganism onto the first or second water-swellable gelling agent to form an inoculated device, laminating the first layer back to the second layer, and incubating the inoculated device.

In a fourth aspect, a kit is provided. The kit includes at least one device according to the first aspect and instructions for detecting and enumerating at least one microorganism in a sample using the device(s).

The devices and methods allows for simple and rapid detection of microorganisms.

While the above-identified drawings, which may not be drawn to scale, set forth various embodiments of the present disclosure, other embodiments are also contemplated, as noted in the detailed description.

DETAILED DESCRIPTION

Devices and methods of propagating or storing a microorganism are provided, as are kits and methods of making the devices.

The recitation of any numerical range by endpoints is meant to include the endpoints of the range, all numbers within the range, and any narrower range within the stated range (e.g. 1 to 5 includes 1, 1.5, 2, 2.75, 3, 3.8, 4, and 5). Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example, the expression "A and/or B" means A, B, or a combination of A and B.

"Agglomerated" refers to a weak association of primary particles or aggregated particles usually held together by charge or polarity. Agglomerated particles can typically be broken down into smaller entities by, for example, shearing forces encountered during dispersion of the agglomerated particles in a liquid. The terms "aggregated" and "aggregates" refer to a strong association of primary particles often bound together by, for example, residual chemical treatment, covalent chemical bonds, or ionic chemical bonds. Further breakdown of the aggregates into smaller entities is very difficult to achieve.

"Cold-water-soluble" refers to material which forms a solution in water at room temperature (i.e., about 25° C.).

"Hydrophobic" refers to a material that exhibits a water contact angle of 90° or larger on its surface.

"Opaque" refers to a substrate having at most 10% light transmission.

"Powder" refers to a finely divided particulate material having an average diameter in a range from 0.1 micrometer up to 400 micrometers.

"Transparent" refers to a substrate having at least 90% light transmission.

Devices for the propagation and/or storage of microorganisms are provided having advantageous features such as increased resistance to organism metabolism (e.g., liquefying bacteria), and ionizing radiation for decontamination or sterilization (e.g., gamma radiation, e-beam radiation, etc.).

In a first aspect, a device is provided. More particularly, a device is provided including a first layer that has a first portion of a surface of the first layer, to which a first water-swellable gelling agent comprising a first clay is affixed. The device further includes a second layer that is separable from the first layer and has a first portion of a surface of the second layer, to which a second water-swellable gelling agent is affixed.

Figure 1:
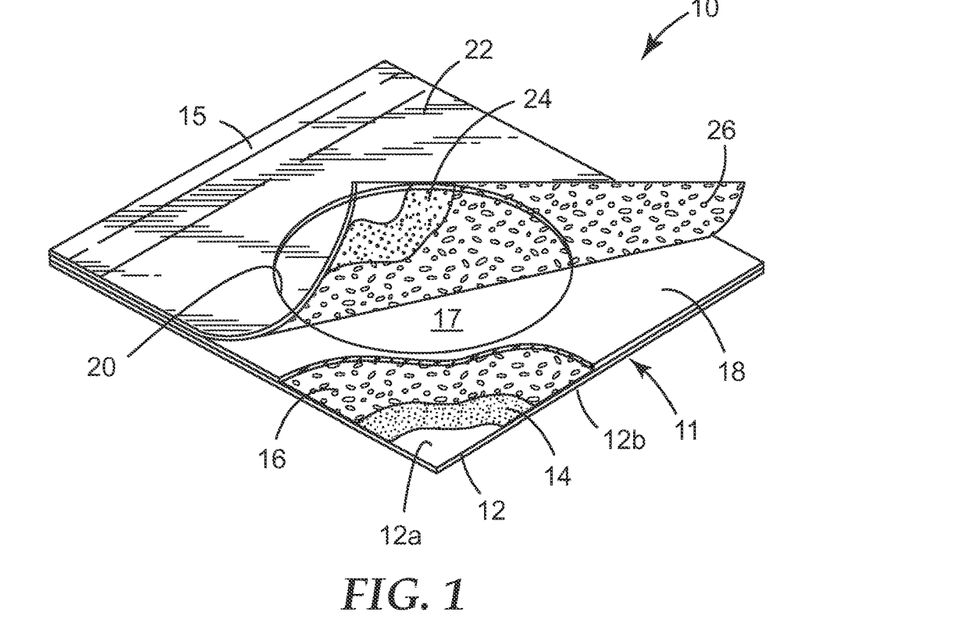
FIG. 1 is a top perspective view, partially in section, of an exemplary embodiment of a microbiological growing device.
Figure 2:
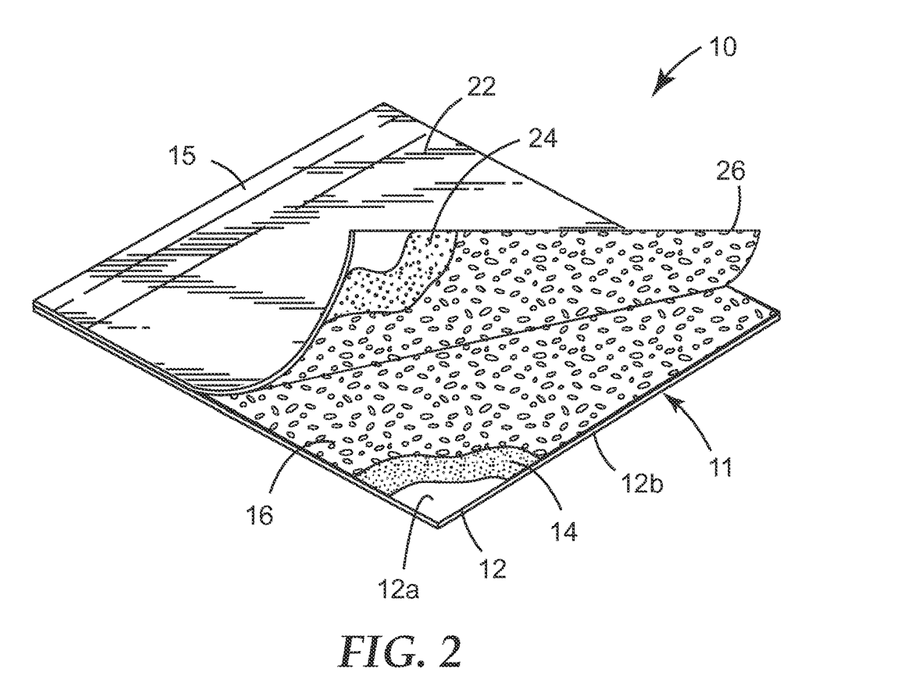
FIG. 2 is a top perspective view, partially in section, of an exemplary embodiment of a microbiological growing device.
Figure 4:
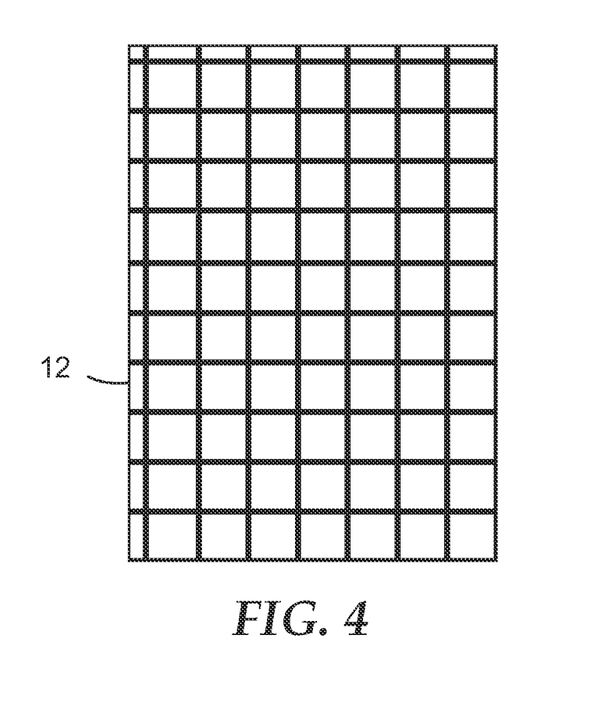
FIG. 4 is a top view of the device of FIG. 2 showing a grid pattern printed on the substrate layer.

FIG. 1 illustrates an exemplary embodiment of device for growing microorganisms. Device 10 includes a body member 11 comprising a first layer (e.g., substrate) 12 having an upper surface 12a and a lower surface 12b. The first layer is typically a self-supporting water-proof substrate. In some embodiments, the first layer 12 is a relatively stiff film of a material such as polyester, polypropylene, silicone, or polystyrene, which will not absorb or otherwise be affected by water. Polyester films having a thickness from about 100 micrometers to about 178 micrometers, and polypropylene films having a thickness from about 100 micrometers to about 200 micrometers, as well as polystyrene films having a thickness of about 380 micrometers have each been found to be suitable for the first layer 12. Other suitable substrates include paper with a polyethylene or other water-proof coating. An example of a suitable polyethylene-coated paper substrate is "Schoeller Type MIL" photoprint paper (commercially available from Schoeller Pulaski, New York). The first layer 12 may be either transparent or opaque, depending on whether one wishes to view bacterial colonies through the substrate. In the exemplary embodiment shown in FIG. 4, the first layer 12 has a square grid pattern printed on lower surface 12b to facilitate the counting of bacterial colonies.

The upper surface 12a comprises a first portion 17, to which a first water-swellable gelling agent 16 comprising a clay is affixed. The clay is typically affixed to the first portion 17 of the upper surface 12a in a uniform layer for easy hydration, using a layer of adhesive 14. The first water-swellable gelling agent 16 includes the clay and optionally a microbial growth nutrient (and may include other additives). In many embodiments, the first water-swellable gelling agent is provided in the form of a powder. The layer of adhesive 14 is water-insoluble and non-inhibitory to the growth of microorganisms. In some embodiments, the adhesive 14 is sufficiently transparent when wet to enable the viewing of bacterial colonies through the film coated with the adhesive. In some embodiments, the adhesive 14 is a pressure-sensitive adhesive. In some other embodiments, heat-activated adhesives in which a lower melting substance is coated onto a higher melting substance may also be used. Water-activated adhesives such as mucilage may also be useful.

A uniform layer of powder 16 is desired with sufficient surface area exposed for hydration. Typically, an adhesive layer in the thickness range from about 5 micrometers to about 50 micrometers is suitable.

Suitable adhesives are transparent when wetted with water. Examples of suitable adhesives include a pressure sensitive adhesive, such as a copolymer of isooctylacrylate/acrylamide in a mole ratio of 94:6 or 95:5. Suitable adhesives may also include those described in U.S. Pat. Nos. 4,565,783, 5,089,413, 5,681,712, and 5,232,838. In some embodiments, silicone pressure sensitive adhesives may be used, including for example those described in U.S. Pat. Nos. 7,695,818 and 7,371,464.

Figure 5:
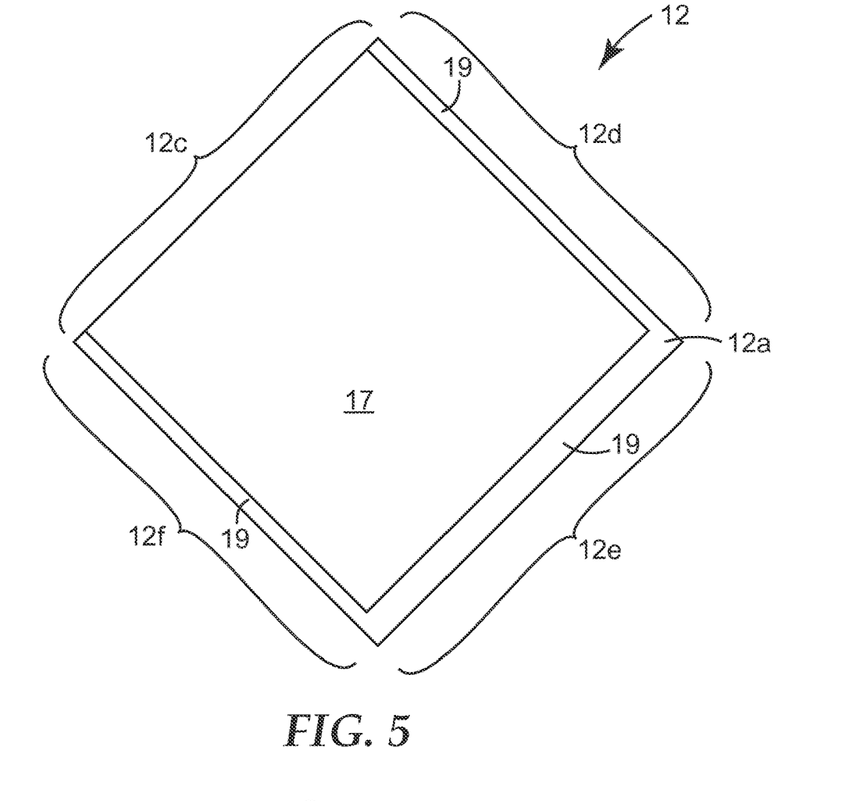
FIG. 5 is a top perspective view of an exemplary embodiment of a layer of a microbiological growing device.

In certain embodiments, as illustrated for instance in FIG. 1, essentially all of the upper surface of the first layer is coated with adhesive. In other embodiments, the first portion of the first layer is coated with an adhesive and a second portion of the surface of the first layer is essentially free of the adhesive. Referring to FIG. 5, an exemplary first layer 12 is provided having a first portion 17 of the upper surface 12a of the first layer 12. A second portion 19 of the upper surface 12a of the first layer 12 at least partially surrounds the first portion 17. The first layer 12 includes a perimeter formed by four edges of the first layer: edge 12c, edge 12d, edge 12e, and edge 12f. In this exemplary embodiment, the first portion 17 is surrounded on three sides by the second portion 19, and thus the second portion 19 is in contact with at least some of the perimeter of the first layer 12, namely edges 12d, 12e, and 12f. The adhesive 14 can be coated on the first portion 17 but not on the second portion 19, using a technique such as pattern coating of the adhesive. Pattern coating of adhesives can be performed as known in the art, for instance as described in PCT Patent Publication WO96/15715 (Yasis et al.). In certain embodiments, the second portion of the first layer substantially surrounds the first portion of the first layer. For instance, the first portion optionally has a (regular or irregular) shape such as circular, quadrilateral, etc., contained entirely within the second portion, which is in contact with the entire perimeter of the first layer. This is illustrated, for instance, in FIG. 1.

Referring again to FIG. 1, the device 10 further includes a second layer 22 (e.g., cover sheet) that is releasably adhered to one edge of the upper surface 12a of the first layer 12. In the present disclosure, the second layer 22 is usually selected to be transparent, in order to facilitate counting of microbial colonies, and is typically also selected to be impermeable to bacteria and have low moisture vapor transmission rate (i.e., the second layer 22 prevents undesired contamination of the dehydrated medium during shipping, storage and use of the devices and provides an environment which will support the growth of microorganisms during the incubation period). In some embodiments, the second layer 22 has the same properties (e.g., stiffness) as the first layer 12, but need not be as stiff. The second layer 22 can be selected to provide the amount of oxygen transmission necessary for the type of microorganism desired to be grown. For example, some polyester films have low oxygen permeability (less than 5 g/645 cm$^2$/24 hours per 25 micrometers of thickness) and would be suitable for growing anaerobic bacteria. On the other hand, some polyethylenes have high oxygen permeability (e.g., approximately 500 g/645 cm$^2$/24 hours per 25 micrometers of thickness) and would be suitable for aerobic organisms. Suitable material for the second layer 22 includes polypropylene, polyester, polyethylene, polystyrene, or silicone. In certain embodiments, the second layer 22 comprises oriented polypropylene, such as biaxially oriented polypropylene, which in some exemplary embodiments has a thickness of about 40 micrometers.

Figure 7:
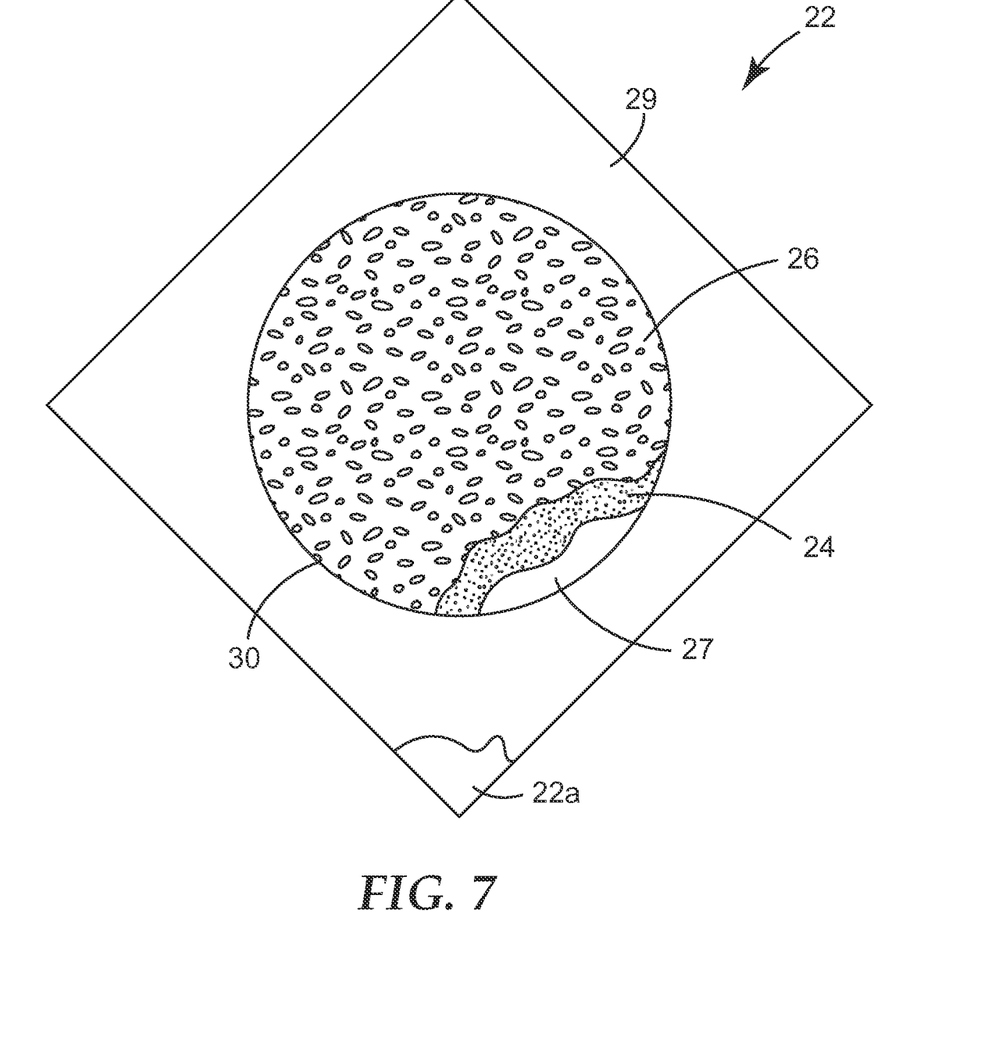
FIG. 7 is a top view, partially in section, of an exemplary embodiment of a layer of a microbiological growing device.

Referring to FIG. 7, similar to the first layer 12, the second layer 22 includes an upper surface 22a that comprises a first portion 27, to which a second water-swellable gelling agent 26 comprising a clay is affixed. The clay is typically affixed to the first portion 27 of the upper surface 22a in a uniform layer for easy hydration using a layer of adhesive 24. The second water-swellable gelling agent 26 includes the clay and optionally a microbial growth nutrient (and may include other additives). In many embodiments, the second water-swellable gelling agent is provided in the form of a powder. The layer of adhesive 24 is water-insoluble and non-inhibitory to the growth of microorganisms. The adhesive 24 is any of the suitable adhesives discussed above with respect to adhesive 14. The adhesive 24 is typically coated onto the second layer 22 in a thickness which is less than the diameter of the particles of the second water-swellable gelling agent 26, in order to adhere the particles of the water-swellable gelling agent 26 to the layer without completely embedding the particles in the adhesive. A uniform layer of the water-swellable gelling agent 26 is desired with sufficient surface area exposed for hydration.

In some embodiments essentially all of the upper surface 22a of the second layer 22 is coated with adhesive. In other embodiments, the first portion 27 of the second layer 22 is coated with an adhesive and a second portion 29 of the surface of the first layer is essentially free of the adhesive. When the adhesive 24 is coated on the first portion 27 but not on the second portion 29, this can be accomplished using a technique such as pattern coating of the adhesive. In certain embodiments, the second portion of the first layer substantially surrounds the first portion of the first layer.

For each of the first layer 12 and the second layer 22, a layer of a water-swellable gelling agent 16, 26 is adhered uniformly to the adhesive layer 14, 24, respectively. The water-swellable gelling agent 16, 26 includes a clay, and optionally one or more microbial growth nutrients for growing microorganisms mixed in with the clay. In certain embodiments, the first gelling agent 16 comprises the same clay as the second gelling agent 26, whereas in other embodiments the second gelling agent 26 includes a second clay that is different from the first clay in the first gelling agent 16. The cold-water-swellability of the water-swellable gelling agent employed in the devices of the present disclosure may result, for example, from the inclusion in these powders of an appropriate clay. Suitable clays for inclusion in water-swellable powder 16 include both natural and synthetic clays which form solutions in water at room temperature without requiring mixing. In many embodiments, the particles of the clay have a platelet shape including one or more stacked layers providing generally flat opposing major surfaces, the layers each having a primarily ellipsoidal shape.

Clays such as synthetic and natural hectorite form solutions in water at room temperature and are suitable gelling agents for providing powders which are water-swellable. Hectorite is a member of the smectite group, and has the formula of $Na_{0.3}(Mg,Li)_3Si_4O_{10}(OH)_2$. In some embodiments the water-swellable gelling agent 16 includes unmodified hectorite and/or organic-modified hectorite, these gelling agents being useful individually or in combination with one another. Some suitable commercially available hectorite clays include organic-modified synthetic hectorite available under the tradename LAPONITE EP, and unmodified synthetic hectorite available under the tradenames LAPONITE RD and LAPONITE XLG, all available from BYK-Chemie GmbH, (Wesel, Germany). In many embodiments, the clay includes particles of a sub-micron size. More particularly, sub-micron size particles include particles having an average particle size, which refers to the average longest dimension of the particles, that is no greater than 1000 nanometers, no greater than 500 nanometers, no greater than 200 nanometers, no greater than 100 nanometers, no greater than 75 nanometers, or no greater than 50 nanometers. The average particle size is often determined using transmission electron microscopy but various light scattering methods (e.g., laser diffraction) can be used as well. The average particle size typically refers to the average size of non-agglomerated and/or non-aggregated single clay particles.

In some embodiments, a water-swellable gelling agent may comprise only a clay gelling agent. Where the device, as manufactured, contains a powder comprising only a clay gelling agent, the end user typically adds special nutrients tailored to the type of microorganisms to be grown. For example, dry powdered nutrients may be suspended in a rapidly-evaporating liquid such as ethanol. In other instances, dry powdered nutrients may be suspended or dissolved in aqueous solutions. An aliquot of the liquid is added to the surface of the first layer 12 or the second layer 22, which has been coated previously with adhesive and gelling agent. The liquid is then allowed to evaporate, leaving ample nutrients along with the gelling agent. In another embodiment, the water-swellable gelling agent 16, 26, may comprise nutrients suitable for growing microorganisms in the device, which form solutions in water at room temperature.

Figure 6:
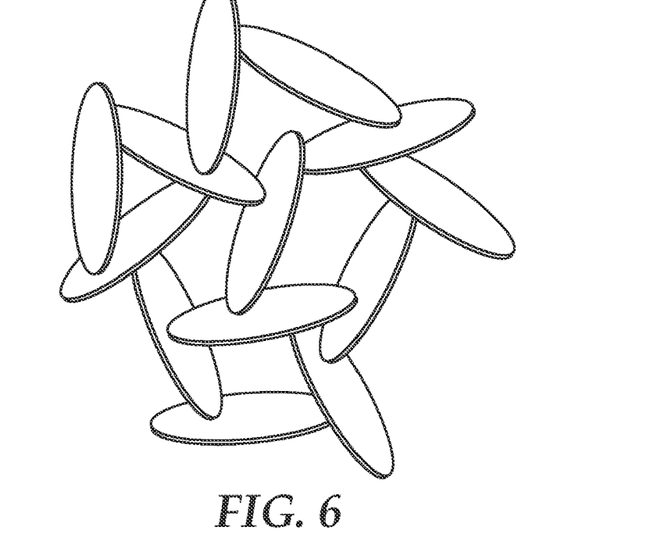
FIG. 6 is a schematic of the structure of a gelled hectorite clay.

Clay minerals (e.g., layered silicate minerals) have been employed in culture devices in which the clays are thoroughly blended with a fluid (e.g., water) to form a slurry, autoclaved, then poured into a petri plate, test tube, or other suitable container for culturing microorganisms. (As described, for instance, in U.S. Pat. No. 1,520,217.) The time required for dispersed clay particles to gel differs from clay to clay. Hectorite particles form a gel when the particles arrange to form a "house of cards" type structure. A schematic illustration of the general gel structure for hectorite is provided in FIG. 6, in which the short edge of one particle aligns with a major surface of another particle, and the plurality of particles collectively form a structure having spaces between the major surfaces of adjacent particles. It has been found that in devices according to the present disclosure, certain clays affixed to a substrate form a gel when hydrated, without requiring any mixing or other physical dispersion (e.g., spreading) following hydration to induce the particles to form a gel. In contrast, certain other clays affixed to a substrate according to the disclosure above do not form a gel when hydrated, for example montmorillonite, organic-modified bentonite, or inorganic-modified synthetic hectorite.

Upon hydration, the water-swellable gelling agent comprising a clay tends to wick out towards the perimeter of the substrate to which it is attached. To minimize the hydration of the clay beyond the perimeter of the substrate and thus out of the device, in many embodiments the second portion of the substrate layer comprises a material that is more hydrophobic than the hydrated clay. The second portion is optionally the material of the layer itself, an adhesive on the layer, a release liner, a dam, or a combination thereof.

In the exemplary embodiment shown in FIG. 1, the body member 11 includes a hydrophobic dam 18 applied to the upper surface 12a of the first layer 12. The hydrophobic dam 18 has a circular aperture 20 cut through its center to expose the first water-swellable gelling agent 16 on the first portion 17 of the upper surface 12a of the first layer 12. The aperture 20 and the first portion 17 are substantially coincident on the upper surface 12a of the first layer 12. The walls of the aperture 20 provide an area of predetermined size and shape to confine the medium following hydration, thus decreasing or preventing wicking of the hydrated gelling agent to or beyond the perimeter of the first layer. The dam 18 can be thick enough to form a well of a desired volume (e.g., 1 milliliter or 2 milliliters). Closed cell polyethylene foam, polyethylene, polydimethylsiloxane (PDMS), or polystyrene, is typically used for the hydrophobic dam 18, but any material that is hydrophobic (i.e., non-wetting by water), inert to microorganisms, and capable of withstanding sterilization may be used. A suitable alternate hydrophobic material is a liner, which does not provide a well in the device, typically made of a thermoplastic material or paper having a hydrophobic coating such as silicone, fluorosilicone, PTFE, or other typical release coating.

In FIG. 1, the second layer 22 is coated on a major surface thereof with a layer of adhesive 24 and layer of a coating composition 26. The major surface of second layer 22 having the layer of coating composition 26 faces the upper surface 12a of the substrate 12. The layer of adhesive 24 is water-insoluble and non-inhibitory to the growth of microorganisms, and is sufficiently transparent when wet to enable the viewing of gas bubbles or microbial colonies through the film coated with the adhesive. In some embodiments, the layer of adhesive 24 comprises a pressure-sensitive adhesive. A uniform layer of the coating composition 26 is desired with sufficient surface area exposed for hydration.

Referring to FIG. 7, in an exemplary embodiment a hydrophobic dam 28 is applied to the upper surface 22a of the second layer 22, the hydrophobic dam 28 having a circular aperture 30 cut through its center to expose the second water-swellable gelling agent 26 on the first portion 27 of the upper surface 22a of the second layer 22. The aperture 30 and the first portion 27 are substantially coincident on the upper surface 22a of the second layer 22. The walls of the aperture 30 provide an area of predetermined size and shape to confine the medium following hydration, thus decreasing or preventing wicking of the hydrated gelling agent to or beyond the perimeter of the second layer. Alternatively, a release liner could be used in place of the hydrophobic dam 28. The dam and release liner typically include the materials disclosed above with respect to the dam and release liners used with the first layer.

In certain embodiments, the water-swellable gelling agent contains clay as the sole water-swellable gelling agent, whereas in others the water-swellable gelling agent contains one or more organic cold-water-soluble agents, such as guar gum, xanthan gum, hydroxyethyl cellulose, carboxymethyl cellulose, polyacrylamide, locust bean gum and algin. Such organic cold-water-soluble agents form solutions in water at room temperature and are suitable gelling agents for including in the first water-swellable gelling agent with the clay. In some embodiments the organic cold-water-soluble agents are guar gum and xanthan gum, these gelling agents being useful individually or in combination with one another, mixed with the clay. In some embodiments, the powdered gelling agent comprises up to 75% by weight of an additional water-swelling agent and/or organic cold-water-soluble gelling agent, or up to 50% by weight, or up to 25% by weight of an additional water-swelling agent and/or organic cold-water-soluble gelling agent; such as between 1% and 75% by weight of an additional water-swelling agent and/or organic cold-water-soluble gelling agent, or between 50% and 75%, or between 10% and 50% by weight of an additional water-swelling agent and/or organic cold-water-soluble gelling agent. Optionally, the powdered water-swellable gelling agent may further comprise an inducer, and indicator, or a combination of these.

Non-limiting examples of nutrients, additional gelling agents, and mixtures thereof for supporting growth of microorganisms in a device of the present disclosure include those described in U.S. Pat. Nos. 4,565,783; 5,089,413; 5,232,838; 5,364,766; 5,443,963; 5,462,860; 5,601,998; 5,635,367; and 5,681,712; these references also include non-limiting examples of indicators (e.g., detection reagents) and inducers. For instance, one suitable indicator is triphenyl tetrazolium chloride (TTC). It has been discovered that hectorite clays adsorb TTC, thus a high concentration of TTC can be employed as an indicator at concentrations that typically would be harmful or fatal to microorganisms, such as in an amount of at least 0.5 milligrams per square centimeter of the substrate portion on which it is affixed.

Accordingly, in certain embodiments the device 10 includes a first layer 12 that has a first portion 17 of a surface 12a of the first layer 12, to which a first water-swellable gelling agent 16 comprising a first clay is affixed. The device 10 further includes a second layer 22 that is separable from the first layer and has a first portion 27 of a surface 22a of the second layer 22, to which a second water-swellable gelling agent 26 is affixed.

An advantage of devices according to the present disclosure is that the clay is resistant to damage from high energy radiation, thus the devices can be readily decontaminated or sterilized. In certain embodiments, the device is decontaminated or sterilized by ionizing radiation, such as e-beam radiation or gamma radiation. More particularly, the device may be decontaminated or sterilized by subjection to a dose of ionizing radiation of at least 10 kiloGrays (kgy), or at least 20 kgy, or at least 30 kgy, or at least 40 kgy, or between 10 kgy and 50 kgy, or between 20 kgy and 50 kgy, or up to 50 kgy.

In a second aspect, a method for making a device for the propagation or storage of microorganisms is provided. The method for making the device includes providing a first layer having a surface; affixing a first water-swellable gelling agent including a first clay to a first portion of the surface of the first layer; providing a second layer having a surface; and affixing a second water-swellable gelling agent to a first portion of the surface of the second layer. The method further includes laminating the first layer to the second layer, in which the first water-swellable gelling agent at least partially contacts the second water-swellable gelling agent.

The water-swellable gelling agent is affixed to each of the first layer and the second layer by any suitable method. In some embodiments, affixing the (first or second) water-swellable gelling agent to the (first or second, respectively) layer includes disposing a layer of an adhesive on the surface of the layer, disposing a material that is more hydrophobic than the first clay over a second portion of the layer, and coating the adhesive layer with the water-swellable gelling agent. The material thus acts as a mask to prevent coating the water-swellable gelling agent onto the second portion of the layer. This method often further includes removing the material from the second portion of the layer prior to laminating the first layer to the second layer, but the material can also be left in the device between the first and second layers. In some embodiments, affixing the (first or second) water-swellable gelling agent to the (first or second, respectively) layer includes disposing a layer of an adhesive on the first portion of the surface of the layer, and coating the adhesive layer with the water-swellable gelling agent. This method usually further includes removing at least some of the water-swellable gelling agent disposed on a second portion of the surface of the layer. The water-swellable gelling agent disposed on the second portion will typically not be affixed to the surface of the layer due to a lack of adhesive on the second portion.

The devices prepared by the methods of the second aspect will advantageously have a hydrophobic material on/as the second portion of at least one of the two substrate layers to minimize wicking of the hydrated gelling agent beyond the edges of the device. The materials, configurations, etc. described in detail above with respect to the first aspect are suitable for the devices made by the methods of the second aspect.

In a third aspect, a method of detecting and enumerating at least one microorganism in a sample is provided. The method includes providing a device according to the first aspect, separating the first layer from the second layer, adding an aliquot of a sample containing at least one microorganism onto the first or second water-swellable gelling agent to form an inoculated device, laminating the first layer back to the second layer, and incubating the inoculated device. Any of the devices described in detail above with respect to the first aspect are suitable for use in the methods of the third aspect.

Figure 3:
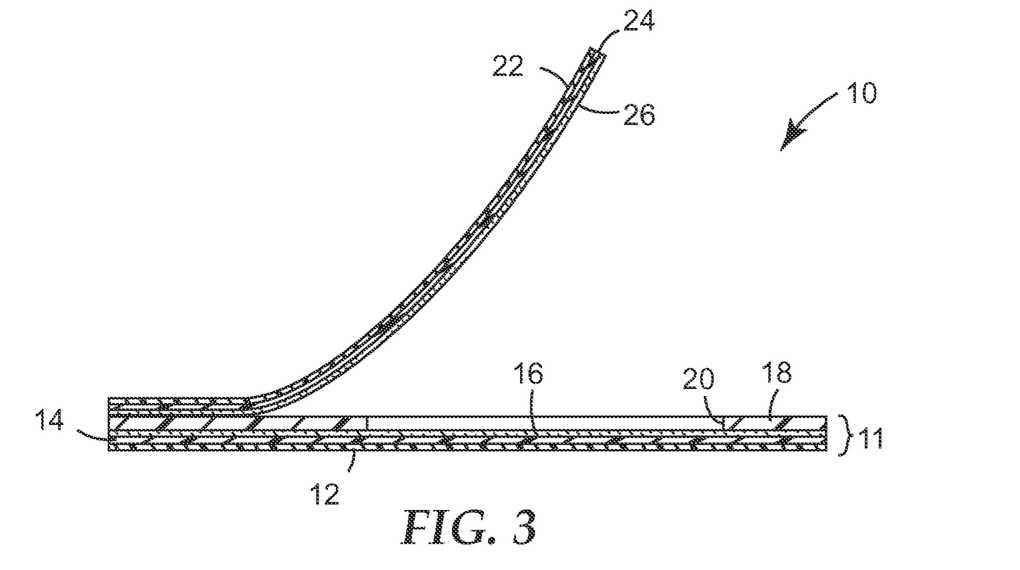
FIG. 3 is a cross sectional view of the device of FIG. 1.

For instance, the use of the devices of the present invention for detecting and enumerating microorganisms can be discussed with specific reference to the device of FIGS. 1 and 3. In certain embodiments, the second layer 22 acts as a cover sheet and is pulled back, and then a predetermined quantity of water or an aqueous test sample is placed on the first layer 12 of the body member 11. The particles of the gelling agent 16 adhered to the first layer 12 by the adhesive 14 are quickly hydrated or dissolved and a gel is formed. The second layer 22 is then replaced over the first layer 12 carefully, in order to minimize entrapment of air bubbles. The device is then incubated for a predetermined period of time. The inoculated device typically includes incubating for up to about 48 hours, or up to about 24 hours, or even up to about 14 hours. Any bacterial colonies growing in the medium can be detected and optionally enumerated (e.g., counted) through the transparent cover film. In some embodiments, the microorganisms can be counted using an automated system, such as an automated colony counter.

Generally, a single aliquot of sample is added onto the first water-swellable gelling agent or the second water-swellable gelling agent, although it is possible to add more than one aliquot if needed. In many embodiments, the gelling agent is advantageously not mixed after adding the aliquot before laminating the first layer back to the second layer. As discussed above, the clay is selected to gel following hydration without requiring mixing or spreading.

In a fourth aspect, a kit is provided. The kit includes at least one device according to the first aspect and instructions for detecting and enumerating at least one microorganism in a sample using the device(s). Any of the devices described in detail above with respect to the first aspect are suitable for use in the kit of the fourth aspect. The kit optionally further includes an aqueous fluid, such as water or a buffer solution, for a user to employ with the devices. Moreover, the kit may also include one or more microbial growth nutrient(s), indicator(s), inducer(s), or combinations thereof. In particular, when a user would desire to tailor a microbial growth nutrient for a specific microorganism, for example, having the microbial growth nutrient provided in a kit separately from the device can be convenient.

Various embodiments are described that are devices, kits, methods of making the devices, or methods of detecting and enumerating microorganisms.

Embodiment 1 is a device for the propagation or storage of microorganisms. The device includes a) a first layer that comprises a first portion of a surface of the first layer, to which a first water-swellable gelling agent including a first clay is affixed. The device further includes b) a second layer that is separable from the first layer and comprises a first portion of a surface of the second layer, to which a second water-swellable gelling agent is affixed.

Embodiment 2 is the device of embodiment 1, wherein the first layer further comprises a second portion of the surface.

Embodiment 3 is the device of embodiment 1 or embodiment 2, wherein the second layer further comprises a second portion of the surface.

Embodiment 4 is the device of any of embodiments 1 to 3, wherein the second water-swellable gelling agent includes a second clay.

Embodiment 5 is the device of embodiment 4, wherein the first clay and the second clay are the same clay.

Embodiment 6 is the device of embodiment 4, wherein the first clay and the second clay are different clays.

Embodiment 7 is the device of any of embodiments 1 to 6, wherein the first clay includes sub-micron sized particles.

Embodiment 8 is the device of any of embodiments 1 to 7, wherein the first clay includes at least one platelet shape.

Embodiment 9 is the device of any of embodiments 1 to 8, wherein the first gelling agent further includes a microbial growth nutrient.

Embodiment 10 is the device of any of embodiments 1 to 9, wherein the device is decontaminated.

Embodiment 11 is the device of any of embodiments 1 to 10, wherein the device is sterilized.

Embodiment 12 is the device of any of embodiments 1 to 11, wherein the device is sterilized with ionizing radiation.

Embodiment 13 is the device of embodiment 12, wherein the device is sterilized with gamma radiation or e-beam radiation.

Embodiment 14 is the device of any of embodiments 1 to 13, further including an indicator disposed on the first layer, the second layer, or both.

Embodiment 15 is the device of embodiment 14, wherein the indicator includes triphenyl tetrazolium chloride (TTC) in an amount of at least 0.5 mg/cm$^2$.

Embodiment 16 is the device of any of embodiments 1 to 15, further including an inducer disposed on the first layer, the second layer, or both.

Embodiment 17 is the device of any of embodiments 1 to 16, wherein the first water-swellable gelling agent is affixed to the first layer by an adhesive.

Embodiment 18 is the device of any of embodiments 1 to 17, wherein the first water-swellable gelling agent is affixed to the first layer by a pressure sensitive adhesive.

Embodiment 19 is the device of embodiment 17 or embodiment 18 wherein the adhesive is disposed on the first portion only of the surface of the first layer.

Embodiment 20 is the device of any of embodiments 2 to 19, wherein the second portion of the first layer includes a material that is more hydrophobic than the first clay.

Embodiment 21 is the device of any of embodiments 2 to 20, wherein the second portion of the first layer comprises the first layer, an adhesive, a release liner, a dam, or a combination thereof.

Embodiment 22 is the device of any of embodiments 1 to 21, wherein the second water-swellable gelling agent is affixed to the second layer by an adhesive.

Embodiment 23 is the device of any of embodiments 1 to 22, wherein the second water-swellable gelling agent is affixed to the second layer by a pressure sensitive adhesive.

Embodiment 24 is the device of embodiment 22 or embodiment 23 wherein the adhesive is disposed on the first portion only of the surface of the second layer.

Embodiment 25 is the device of any of embodiments 3 to 24, wherein the second portion of the second layer comprises the second layer, an adhesive, a release liner, a dam, or a combination thereof.

Embodiment 26 is the device of embodiment 21 or embodiment 25, wherein the dam comprises polyethylene, polydimethylsiloxane (PDMS), or polystyrene.

Embodiment 27 is the device of any of embodiments 1 to 26, wherein the first layer comprises polypropylene, polyester, polystyrene, or polyethylene-coated paper.

Embodiment 28 is the device of embodiment 27, wherein the first layer comprises polyethylene-coated paper.

Embodiment 29 is the device of any of embodiments 1 to 28, wherein the second layer comprises polypropylene, polyester, polyethylene, polystyrene, or silicone.

Embodiment 30 is the device of embodiment 29, wherein the second layer comprises oriented polypropylene.

Embodiment 31 is the device of any of embodiments 1 to 30, wherein the second water-swellable gelling agent affixed to the second layer further includes a microbial growth nutrient.

Embodiment 32 is the device of any of embodiments 2 to 31, wherein the first layer further comprises a perimeter and the second portion of the surface is in contact with at least some of the perimeter of the first layer.

Embodiment 33 is the device of embodiment 32, wherein the second portion of the first layer substantially surrounds the first portion of the first layer.

Embodiment 34 is the device of any of embodiments 3 to 33, wherein the second layer further comprises a perimeter, and the second portion of the surface is in contact with at least some of the perimeter of the second layer.

Embodiment 35 is the device of embodiment 34, wherein the second portion of the second layer substantially surrounds the first portion of the second layer.

Embodiment 36 is the method of any of embodiments 1 to 35, wherein the first clay includes synthetic hectorite.

Embodiment 37 is the device of any of embodiments 1 to 36, wherein the first clay includes unmodified hectorite, organic-modified hectorite, or a combination thereof.

Embodiment 38 is the device of any of embodiments 1 to 37, wherein the first water-swellable gelling agent, the second water-swellable gelling agent, or both, includes up to 75% by weight of an additional water-swelling agent and/or a cold-water-soluble gelling agent.

Embodiment 39 is the device of any of embodiments 1 to 38, wherein the first water-swellable gelling agent, the second water-swellable gelling agent, or both, includes up to 50% by weight of an additional water-swelling agent and/or an organic cold-water-soluble gelling agent.

Embodiment 40 is the device of any of embodiments 1 to 39, wherein the first water-swellable gelling agent, the second water-swellable gelling agent, or both, includes up to 25% by weight of an additional water-swelling agent and/or an organic cold-water-soluble gelling agent.

Embodiment 41 is the device of any of embodiments 1 to 38, wherein the first water-swellable gelling agent, the second water-swellable gelling agent, or both, includes between 1% and 75% by weight of an additional water-swelling agent and/or an organic cold-water-soluble gelling agent.

Embodiment 42 is the device of any of embodiments 1 to 38, wherein the first water-swellable gelling agent, the second water-swellable gelling agent, or both, includes between 50% and 75% by weight of an additional water-swelling agent and/or an organic cold-water-soluble gelling agent.

Embodiment 43 is the device of any of embodiments 1 to 38, wherein the first water-swellable gelling agent, the second water-swellable gelling agent, or both, includes between 10% and 50% by weight of an additional water-swelling agent and/or an organic cold-water-soluble gelling agent.

Embodiment 44 is a method of making a device for the propagation or storage of microorganisms. The method includes providing a first layer comprising a surface; affixing a first water-swellable gelling agent including a first clay to a first portion of the surface of the first layer; providing a second layer comprising a surface; and affixing a second water-swellable gelling agent to a first portion of the surface of the second layer. The method further includes laminating the first layer to the second layer, wherein the first water-swellable gelling agent at least partially contacts the second water-swellable gelling agent.

Embodiment 45 is the method of embodiment 44, wherein the affixing the first water-swellable gelling agent to the first layer includes disposing a layer of an adhesive on the surface of the first layer; disposing a material that is more hydrophobic than the first clay over a second portion of the first layer, and coating the adhesive layer with the first water-swellable gelling agent.

Embodiment 46 is the method of embodiment 45, further including removing the material from the second portion of the first layer prior to laminating the first layer to the second layer.

Embodiment 47 is the method of embodiment 44, wherein the affixing the first water-swellable gelling agent to the first layer includes disposing a layer of an adhesive on the first portion of the surface of the first layer; and coating the adhesive layer with the first water-swellable gelling agent.

Embodiment 48 is the method of embodiment 47, further including removing at least some of the first water-swellable gelling agent disposed on a second portion of the surface of the first layer.

Embodiment 49 is the method of any of embodiments 44 to 48, wherein the affixing the second water-swellable gelling agent to the second layer includes disposing a layer of an adhesive on the surface of the second layer; disposing a material that is more hydrophobic than the first clay over a second portion of the second layer, and coating the adhesive layer with the first water-swellable gelling agent.

Embodiment 50 is the method of embodiment 49, further including removing the material from the second portion of the second layer prior to laminating the first layer to the second layer.

Embodiment 51 is the method of any of embodiments 44 to 50, wherein the affixing the second water-swellable gelling agent to the second layer includes disposing a layer of an adhesive on the first portion of the surface of the second layer; and coating the adhesive layer with the second water-swellable gelling agent.

Embodiment 52 is the method of embodiment 51, further including removing at least some of the water-swellable gelling agent disposed on a second portion of the surface of the second layer.

Embodiment 53 is the method of any of embodiments 44 to 52, further including decontaminating the device.

Embodiment 54 is the method of any of embodiments 44 to 52, further including sterilizing the device.

Embodiment 55 is the method of embodiment 53 or embodiment 54, wherein the decontaminating or sterilizing includes subjection to ionizing radiation.

Embodiment 56 is the method of any of embodiments 53 to 55, wherein the decontaminating or sterilizing includes gamma irradiation or e-beam irradiation.

Embodiment 57 is the method of any of embodiments 53 to 56, wherein the decontaminating or sterilizing includes subjection to a dose of ionizing radiation of at least 10 kiloGrays (kgy).

Embodiment 58 is the method of any of embodiments 53 to 57, wherein the decontaminating or sterilizing includes subjection to a dose of ionizing radiation of at least 20 kgy.

Embodiment 59 is the method of any of embodiments 53 to 57, wherein the decontaminating or sterilizing includes subjection to a dose of ionizing radiation between 10 kgy and 50 kgy.

Embodiment 60 is the method of any of embodiments 53 to 59, wherein the decontaminating or sterilizing includes subjection to a dose of ionizing radiation of up to 50 kgy.

Embodiment 61 is the method of any of embodiments 44 to 59, wherein the second water-swellable gelling agent includes a second clay.

Embodiment 62 is the method of embodiment 61, wherein the first clay and the second clay are the same clay.

Embodiment 63 is the method of embodiment 61, wherein the first clay and the second clay are different clays.

Embodiment 64 is the method of any of embodiments 44 to 63, wherein the first clay includes sub-micron sized particles.

Embodiment 65 is the method of any of embodiments 39 to 59, wherein the first clay includes at least one platelet shape.

Embodiment 66 is the method of any of embodiments 45, 46, or 48, wherein the second portion of the first layer comprises the first layer, an adhesive, a release liner, a dam, or a combination thereof.

Embodiment 67 is the method of any of embodiments 49, 50, or 52, wherein the second portion of the second layer comprises the second layer, an adhesive, a release liner, a dam, or a combination thereof.

Embodiment 68 is the method of embodiment 66 or embodiment 67, wherein the dam comprises polyethylene, polydimethylsiloxane (PDMS), or polystyrene.

Embodiment 69 is the method of embodiment 66 or embodiment 68, wherein the first layer further comprises a perimeter and the second portion of the surface is in contact with at least some of the perimeter of the first layer.

Embodiment 70 is the method of embodiment 69, wherein the second portion of the first layer substantially surrounds the first portion of the first layer.

Embodiment 71 is the method of embodiment 67 or embodiment 68, wherein the second layer further comprises a perimeter and the second portion of the surface is in contact with at least some of the perimeter of the second layer.

Embodiment 72 is the method of embodiment 71, wherein the second portion of the second layer substantially surrounds the first portion of the second layer.

Embodiment 73 is the method of any of embodiments 44 to 67, wherein the first gelling agent further includes a microbial growth nutrient.

Embodiment 74 is the method of any of embodiments 44 to 68, wherein the device further includes an indicator disposed on the first layer, the second layer, or both.

Embodiment 75 is the method of embodiment 74, wherein the indicator includes triphenyl tetrazolium chloride (TTC) in an amount of at least 0.5 mg/cm$^2$.

Embodiment 76 is the method of any of embodiments 44 to 75, further including an inducer disposed on the first layer, the second layer, or both.

Embodiment 77 is the method of any of embodiments 44 to 76, wherein the first layer comprises polypropylene, polyester, polystyrene, or polyethylene-coated paper.

Embodiment 78 is the method of embodiment 77, wherein the first layer comprises polyethylene-coated paper.

Embodiment 79 is the method of any of embodiments 44 to 78, wherein the second layer comprises polypropylene, polyester, polyethylene, polystyrene, or silicone.

Embodiment 80 is the method of embodiment 79, wherein the second layer comprises oriented polypropylene.

Embodiment 81 is the method of any of embodiments 44 to 80, wherein the second water-swellable gelling agent affixed to the second layer further includes a microbial growth nutrient.

Embodiment 82 is the method of any of embodiments 44 to 81, wherein the first clay includes synthetic hectorite.

Embodiment 83 is the method of any of embodiments 44 to 82, wherein the first clay includes unmodified hectorite, organic-modified hectorite, or a combination thereof.

Embodiment 84 is the method of any of embodiments 44 to 83, wherein the first water-swellable gelling agent, the second water-swellable gelling agent, or both, includes up to 75% by weight of an additional water-swelling agent and/or an organic cold-water-soluble gelling agent.

Embodiment 85 is the method of any of embodiments 44 to 84, wherein the first water-swellable gelling agent, the second water-swellable gelling agent, or both, includes up to 50% by weight of an additional water-swelling agent and/or an organic cold-water-soluble gelling agent.

Embodiment 86 is the method of any of embodiments 44 to 85, wherein the first water-swellable gelling agent, the second water-swellable gelling agent, or both, includes up to 25% by weight of an additional water-swelling agent and/or an organic cold-water-soluble gelling agent.

Embodiment 87 is the method of any of embodiments 44 to 84, wherein the first water-swellable gelling agent, the second water-swellable gelling agent, or both, includes between 1% and 75% by weight of an additional water-swelling agent and/or an organic cold-water-soluble gelling agent.

Embodiment 88 is the method of any of embodiments 44 to 84, wherein the first water-swellable gelling agent, the second water-swellable gelling agent, or both, includes between 50% and 75% by weight of an additional water-swelling agent and/or an organic cold-water-soluble gelling agent.

Embodiment 89 is the method of any of embodiments 44 to 84, wherein the first water-swellable gelling agent, the second water-swellable gelling agent, or both, includes between 10% and 50% by weight of an additional water-swelling agent and/or an organic cold-water-soluble gelling agent.

Embodiment 90 is a method for detecting and enumerating at least one microorganism in a sample including providing a device according to any of embodiments 1 to 43; separating the first layer from the second layer; adding an aliquot of a sample containing at least one microorganism onto the first water-swellable gelling agent or the second water-swellable gelling agent to form an inoculated device; laminating the first layer back to the second layer; and incubating the inoculated device.

Embodiment 91 is the method of embodiment 90, wherein incubating the inoculated device includes incubating for up to about 48 hours.

Embodiment 92 is the method of embodiment 90 or embodiment 91, wherein incubating the inoculated device includes incubating for up to about 24 hours.

Embodiment 93 is the method of any of embodiments 90 to 92, wherein incubating the inoculated device includes incubating for up to about 14 hours.

Embodiment 94 is the method of any of embodiments 90 to 93, further including detecting a microorganism colony in the inoculated device.

Embodiment 95 is the method of any of embodiments 90 to 94, further including enumerating microorganism colonies present in the inoculated device after incubating the inoculated device.

Embodiment 96 is the method of any of embodiments 90 to 95, wherein the first gelling agent is not mixed after adding the aliquot before laminating the first layer back to the second layer.

Embodiment 97 is the method of any of embodiments 90 to 96, wherein the second gelling agent is not mixed after adding the aliquot before laminating the first layer back to the second layer.

Embodiment 98 is the method of any of embodiments 90 to 97, wherein a single aliquot of sample is added onto the first water-swellable gelling agent or the second water-swellable gelling agent.

Embodiment 99 is a kit comprising at least one device according to any of embodiments 1 to 43; and instructions for detecting and enumerating at least one microorganism in a sample using the at least one device.

Embodiment 100 is the kit of embodiment 99, further including an aqueous fluid.

Embodiment 101 is the kit of embodiment 100, wherein the aqueous fluid includes water or a buffer solution.

Embodiment 102 is the kit of any of embodiments 99 to 101, further including a microbial growth nutrient, an indicator, an inducer, or a combination thereof.

Embodiment 103 is the device of any of embodiments 1 to 38, wherein the first water-swellable gelling agent, the second water-swellable gelling agent, or both, is present in the form of a powder.

Embodiment 104 is the method of any of embodiments 44 to 98, wherein the first water-swellable gelling agent, the second water-swellable gelling agent, or both, is present in the form of a powder.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals are available from chemical suppliers such as Sigma-Aldrich Chemical Company, St. Louis, Mo.

Example 1

Device Constructions

Figure 8A:
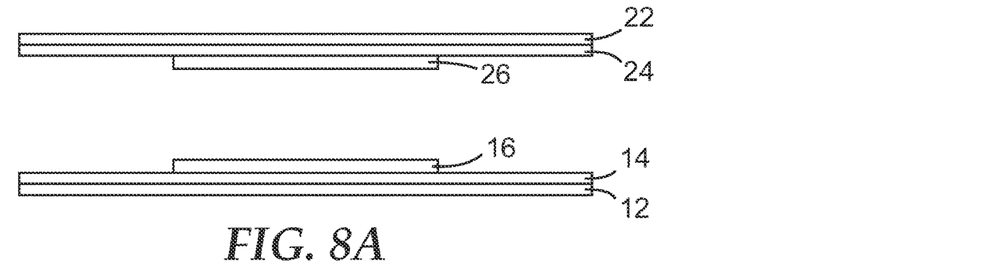
FIG. 8A is a cross-section schematic of an exemplary embodiment of a microbiological growing device.
Figure 8B:
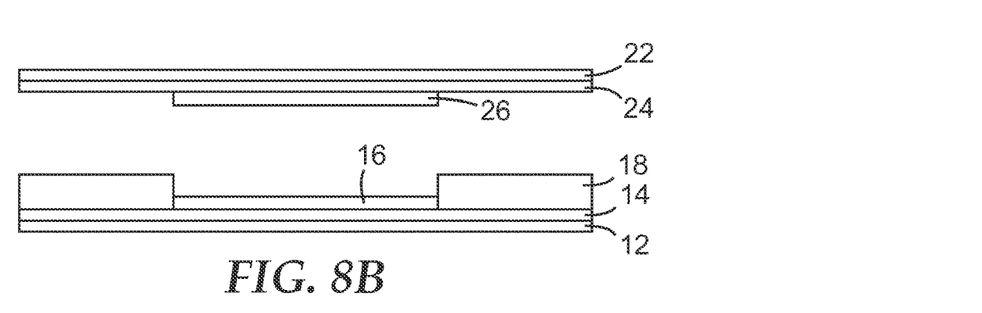
FIG. 8B is a cross-section schematic of another exemplary embodiment of a microbiological growing device.
Figure 8C:
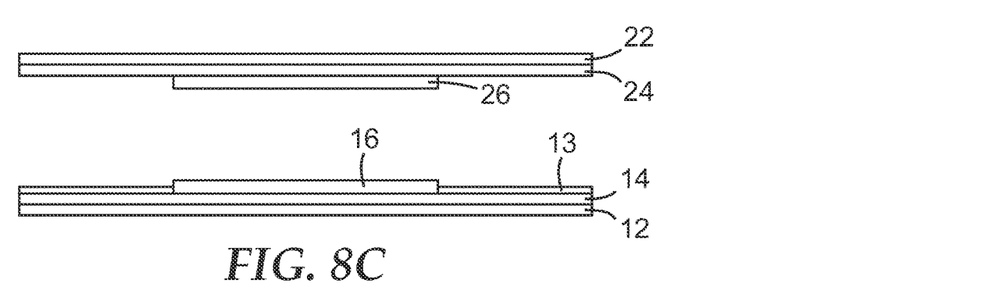
FIG. 8C is a cross-section schematic of a further exemplary embodiment of a microbiological growing device.
Figure 8D:
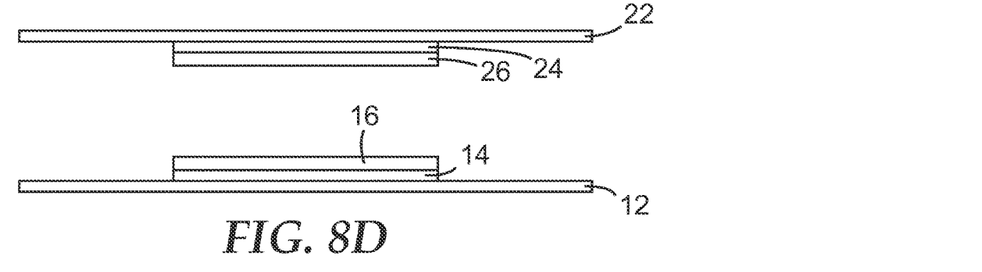
FIG. 8D is a cross-section schematic of a still further exemplary embodiment of a microbiological growing device.

Referring to FIGS. 8A-8C, 1.6 mil biaxially-oriented polypropylene (BOPP) films 12, 22 coated with an isooctyl acrylate/acrylamide pressure sensitive adhesive (PSA) containing triphenyl tetrazolium chloride (TTC) 14, 24 were made as described in Example 1 of U.S. Pat. No. 5,409,838. A silicone coated paper release liner (such as; D#63 BL KFT H/O 548440/000; Loprex GmbH, Stuttgart, Germany) with a 6 centimeter diameter circle removed was used to mask the adhesive 14, 24 on sheets of a first layer 12 and second layer 22, respectively. Exposed adhesive was powder coated with a clay (e.g. LAPONITE EP, BYK Additives Inc., Gonzales, Tex.) 16, 26. The powder was evenly applied and excess powder was removed from the adhesive layer by hand shaking of the film followed by removal of the release liners. For the device of FIG. 8A, nothing further was done. For the device of 8B, a foam spacer (polystyrene foam; 76 mm wide by 102 mm long by 0.57 mm thick) with a circular opening 61 mm in diameter 18 was adhesively laminated to the adhesive coated side of the first layer 12, and for the device of 8C, a fresh silicone coated paper release liner (such as; D#63 BL KFT H/O 548440/000; Loprex GmbH, Stuttgart, Germany) with a circular opening 61 mm in diameter 13 was placed release side away onto the first adhesive coated layer 12. In each of these constructions the wicking of the sample toward the edge of the device is stopped by the hydrophobic adhesive 24 exposed on the second film 22 and also by the foam dam 18 (FIG. 8B) or release liner 13 (FIG. 8C). FIG. 8D illustrates pattern coated adhesive layers made using the same films (1.6 mil BOPP) 12, 22 and adhesives (isooctyl acrylate/acrylamide PSA) 14, 24 as FIGS. 8A-8C. The pattern coated adhesives 14, 24 were then powder coated with gelling agent (LAPONITE EP, BYK Additives Inc., Gonzales, Tex.) 16, 26. The powder on the adhesive free areas of the films was brushed away. The construction of FIG. 8D eliminates the need for complicated constructions with foam dams or release liners.

Example 2

Growth and Detection of Microorganisms in LAPONITE Devices

LAPONITE based culture devices were constructed as in FIG. 8A. *Staphylococcus aureus* (Xen29, Perkin-Elmer) was grown overnight in TSB (Bacto Tryptic soy broth, Becton, Dickinson and Company, New Jersey) shaking at 37° C. A ten-fold dilution series was performed in TSB and 1 ml of each dilution was plated on a separate LAPONITE based culture device. After incubation at 37° C. for 24 hours no red colonies, resulting from the reduction of TTC by the bacteria, were visible. Upon closer inspection colonies of *S. aureus* were visible by the naked eye as small cream to yellow colored irregular circles; they had just not converted the TTC. The experiment was repeated with *Escherichia coli* ATCC #25922 (EZ-CFU, Microbiologics; St. Cloud, Minn.) grown, diluted, and inoculated in the same way as *S. auresus*, but with 40 ug/ml additional TTC (Sigma-Aldrich Chemical Company, St. Louis, Mo.) in the diluent. While red colonies (TTC reduction) were again not observed, colonies of *E. coli* were clearly visible to the naked eye. Colony counts for a given dilution were similar to those obtained by plating 1 ml of that dilution on Aerobic count (AC) PETRIFILM (3M company, St. Paul, Minn.) for both *S. aureus* and *E. coli*. Example 2 demonstrates that microorganisms can be grown and detected by the devices according to the present disclosure.

Example 3

Test of Various Clays as Gelling Agents in Thin Film Culture Devices

LAPONITE based culture devices were constructed as in FIG. 8C using a number of different commercially available clays (Table 1) to determine clay compositions suitable for this application. The top sheet of each device was peeled up from the bottom sheet, and 1 mL of TSB (Bacto Tryptic soy broth, Becton, Dickinson and Company, New Jersey) was applied to the middle of the circle on the bottom sheet. The top sheet was then allowed to roll back into position over the bottom sheet. Wettability was assessed, and "excellent wettability" was defined as complete coverage of the clay surfaces without the need for additional external forces, for example, a plastic spreading device (PETRIFILM yeast and mold plate spreader, 3M Company; St. Paul, Minn.). Time-to-coverage was not measured, but the speed was noted. Gel time was assessed by allowing the inoculated device to sit for 5 minutes and then lifting the sheet by the edge to see if water flowed out of the clay areas. "Excellent gel time" was defined as no noticeable water flowing from the clay surface. Post peel was examined to determine the integrity of the gel slab once formed. If the clay surfaces were not noticeably disturbed by peeling back the top sheet from the bottom, the post peel was defined as excellent.

TABLE 1

Performance of various clays as gelling agents in PETRIFILMS

| Clay Material | Wettability | Gel Time | Post Peel |
| --- | --- | --- | --- |
| LAPONITE EP, BYK Additives Inc., Gonzales, TX | Excellent, fast but not complete | Excellent | Excellent |
| LAPONITE RD BYK Additives Inc., Gonzales, TX | Excellent, even without top sheet roll-down; complete | Excellent | Some disturbance possibly because material not completely gelled yet. |
| LAPONITE XLG BYK Additives Inc., Gonzales, TX | Excellent, even without top sheet roll-down; complete | Excellent | Some disturbance possibly because material not completely gelled yet. |
| LAPONITE XLS BYK Additives Inc., Gonzales, TX | Excellent | None | None |
| Cloisite Na+ (bentonite) BYK Additives Inc., Gonzales, TX | Good | None | None |
| Tixogel VZ BYK Additives Inc., Gonzales, TX | Slow | None | None |

Example 4

Growth and Detection of Microorganisms in LAPONITE Devices Using Indoxyl Based Indicators LAPONITE culture devices were constructed as in FIG. 8C except (1) the bottom film 12 was replaced with a hydrophobic paper (a bleached kraft paper coated with a water-resistance polymeric layer) and (2) the clay powder coat contained 16.6% by weight powdered bacteriological nutrients (A suitable formulation can be found in Table 7 of co-pending U.S. patent application 61/949,631). *Escherichia coli* ATCC #25922 (EZ-CFU, Microbiologics; St. Cloud, Minn.) was grown overnight in TSB (Bacto Tryptic soy broth, Becton, Dickinson and Company, New Jersey) shaking at 37° C. A ten-fold dilution series of the *E. coli* was performed in 9 ml tubes of Butterfield's buffer (3M Company, St. Paul, Minn.) to which 40 ug/ml 5-bromo-4-chloro-3-indolyl-β-D-galactopyranoside (X-gal, Sigma-Aldrich Chemical Company, St. Louis, Mo.) had been added. One ml of each dilution was plated on the LAPONITE device and one ml on a traditional Aerobic Count (AC) PETRIFILM (3M Company, St. Paul, Minn.) and incubated at 37° C. for 24 hours. Colonies were clearly visible as light to dark blue spots (metabolic product of X-gal conversion) and colony counts for a given dilution were similar between the LAPONITE devices and AC PETRIFILM. The above experiment was then repeated exactly except *Staphylococcus aureus* strain 15981 (Valle J et al. Mol Microbiol. 2003 May; 48(4):1075-87) was used and X-gal was replaced with 100 ug/ml 5-bromo-4-chloro-3-indolyl-acetate (Biosynth; Staad, Switzerland). As above, colonies were clearly visible as light to dark blue spots and colony counts for a given dilution were similar between the LAPONITE devices and AC PETRIFILM.

Example 5

Growth and Detection of Microorganisms in LAPONITE Culture Devices Using Fluorescent Indicators LAPONITE culture devices were constructed as in Example 4 without the addition of powdered bacteriological nutrients. *Escherichia coli* ATCC #25922 (EZ-CFU, Microbiologics; St. Cloud, Minn.) was grown overnight in TSB (Bacto Tryptic soy broth, Becton, Dickinson and Company, New Jersey) shaking at 37° C. A ten-fold dilution series of the *E. coli* was performed in Colilert (IDEXX laboratories; Westbrook, Me.) which is a bacteriological medium that contains a fluorescent indicator for *E. coli* (4-Methylumbelliferyl-β-D-glucuronide, concentration is proprietary). One ml of each dilution was plated on the LAPONITE device and after ~14 hours the plates were imaged using a stereomicroscope (Zeiss Luminar V12 with Axiocam MRc5) with a 365 nm excitation line and a 400 nm long pass filter. Colonies were viable as discrete zones with a large amount of fluorescence sequestered in the center. The visualization of individual fluorescent zones with a clearly defined center was surprising because the fluorescent product of bacterial conversion of 4-Methylumbelliferyl-β-D-glucuronide (4-Methylumbelliferone) is soluble and should freely diffuse throughout the plate.

Example 6

Function of LAPONITE Culture Devices after Treatment with Ionizing Radiation

Natural gums are known to break down when exposed to the levels of ionizing radiation (e.g. gamma irradiation or electron beam [e-beam]) required to sterilize manufactured goods. Irradiated natural gums undergo chain scission and lose the ability to form a gel of a given viscosity when hydrated. Clays, on the other hand, are known to be very tolerant to ionizing radiation. Culture devices were constructed as in Example 5, sealed in foil pouches, and exposed to gamma radiation (10, 20, 30, 40, and 50 kgy). *Escherichia coli* ATCC #25922 (EZ-CFU, Microbiologics; St. Cloud, Minn.) was grown overnight in TSB (Bacto Tryptic soy broth, Becton, Dickinson and Company, New Jersey) shaking at 37° C. A ten-fold dilution series of the *E. coli* was performed in 9 ml tubes of TSB (Bacto Tryptic soy broth, Becton, Dickinson and Company, New Jersey) to which 100 ug/ml 5-bromo-4-chloro-3-indolyl-β-D-glucuronide (X-glu, Staad, Switzerland) had been added. One ml of each dilution was plated on the LAPONITE device and one ml on a traditional Aerobic Count (AC) PETRIFILM (3M Company, St. Paul, Minn.) and incubated at 37° C. for 24 hours. Colonies were clearly visible as light to dark blue spots (metabolic product of X-gal conversion) and colony counts for a given dilution were similar between the LAPONITE devices and AC PETRIFILM. The gelling of the LAPONITE based culture devices was unaffected by gamma radiation doses up to and including 50 kgy.

Example 7

Detection of Microbial Growth in LAPONITE Culture Devices Using Elevated Levels of TTC Bottom films were made by coating a hydrophobic paper (a bleached kraft paper coated with a water-resistance polymeric layer) with the isooctyl acrylate/acrylamide pressure sensitive adhesive (PSA) containing triphenyl tetrazolium chloride (TTC) as in Example 1 of U.S. Pat. No. 5,409,838 except that a highly elevated amount of TTC was added such that after coating the adhesive contained 1.59 mg/in$^2$. Bottom films were then coated with a mixture of guar gum (Sigma Aldrich, St. Louis, Mo.) and 16.6% by weight powdered bacteriological nutrients (A suitable formulation can be found in Table 7 of co-pending U.S. patent application 61/949,631). A mask was not placed over the adhesive before powder coating. Top films were constructed as for the top films of FIGS. 8A-C and coated with 100% LAPONITE EP (BYK Additives, Wesel, Germany). A mask was not placed over the adhesive before powder coating. Masking the adhesive and powder coating in a circle is not required for this construction because the guar coated in the bottom film slows down the sample wicking sufficiently to keep the sample inside the culture device. *Escherichia coli* ATCC #25922 and *Staphylococcus aureus* ATCC #25923 (EZ-CFU, Microbiologics; St. Cloud, Minn.) were grown overnight in TSB (Bacto Tryptic soy broth, Becton, Dickinson and Company, New Jersey) shaking at 37° C. A ten-fold dilution series of each organism was performed in 9 ml tubes of Butterfield's buffer (3M Company, St. Paul, Minn.) One ml of each dilution was plated on a LAPONITE device and the top film was simply closed, no spreader was used. Replicate samples were plated on Aerobic Count (AC) PETRIFILM (3M Company, St. Paul, Minn.) for comparison. Plates were incubated at 37° C. for 24 hours. The colony counts from LAPONITE devices with elevated levels of TTC were comparable to the colony counts of Aerobic Count (AC) PETRIFILM (3M Company, St. Paul, Minn.). Example 7 shows the surprising results that hectorite clays adsorb TTC, and thus a high concentration of TTC can be employed as an indicator at concentrations that typically would be harmful or fatal to microorganisms.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A device for the propagation or storage of microorganisms comprising:
    a) a first layer that comprises a first portion of a surface of the first layer, to which a first water-swellable gelling agent comprising a first clay is affixed, wherein the first clay comprises unmodified hectorite, organic-modified hectorite, or a combination thereof and the first layer is a water-proof substrate comprising a polymeric layer or paper with a water-proof coating; and
    b) a second layer that is separable from the first layer and comprises a first portion of a surface of the second layer, to which a second water-swellable gelling agent is affixed.

2. The device of claim 1, wherein the first layer further comprises a second portion of the surface.

3. The device of claim 2, wherein the second portion of the first layer comprises the first layer, an adhesive, a release liner, a dam, or a combination thereof.

4. The device of claim 1, wherein the second water-swellable gelling agent comprises a second clay.

5. The device of claim 1, wherein the first clay comprises at least one platelet shape.

6. The device of claim 1, wherein the device is sterilized with ionizing radiation.

7. The device of claim 1, wherein the first water-swellable gelling agent is affixed to the first layer by an adhesive, wherein the adhesive is disposed on the first portion only of the surface of the first layer.

8. The device of claim 1, wherein the first layer is a water-proof substrate comprising a film of polyester, polypropylene, silicone, or polystyrene.

9. The device of claim 1, wherein the second layer is transparent.

10. A method for detecting and enumerating at least one microorganism in a sample comprising:
providing a device according to claim 1;
separating the first layer from the second layer;
adding an aliquot of a sample containing at least one microorganism onto the first water-swellable gelling agent or the second water-swellable gelling agent to form an inoculated device;
laminating the first layer back to the second layer; and
incubating the inoculated device.

11. The method of claim 10, wherein the first gelling agent is not mixed after adding the aliquot before laminating the first layer back to the second layer.

12. The device of claim 1, further comprising an indicator disposed on the first layer, the second layer, or both, wherein the indicator comprises triphenyl tetrazolium chloride (TTC) in an amount of at least 0.5 mg/cm$^2$.

13. A method of making a device for the propagation or storage of microorganisms comprising:
providing a first layer comprising a surface, wherein the first layer is a water-proof substrate comprising a polymeric layer or paper with a water-proof coating;
affixing a first water-swellable gelling agent comprising a first clay to a first portion of the surface of the first layer, wherein the first clay comprises unmodified hectorite, organic-modified hectorite, or a combination thereof;
providing a second layer comprising a surface;
affixing a second water-swellable gelling agent to a first portion of the surface of the second layer; and
laminating the first layer to the second layer, wherein the first water-swellable gelling agent at least partially contacts the second water-swellable gelling agent.

14. The method of claim 13, wherein the affixing the first water-swellable gelling agent to the first layer comprises disposing a layer of an adhesive on the surface of the first layer; disposing a material that is more hydrophobic than the first clay over a second portion of the first layer, and coating the adhesive layer with the first water-swellable gelling agent.

15. The method of claim 13, wherein the affixing the first water-swellable gelling agent to the first layer comprises disposing a layer of an adhesive on the first portion of the surface of the first layer; and coating the adhesive layer with the first water-swellable gelling agent.

16. The method of claim 15, further comprising removing at least some of the first water-swellable gelling agent disposed on a second portion of the surface of the first layer.

17. The method of claim 13, further comprising decontaminating or sterilizing the device, wherein the decontaminating or sterilizing comprises subjection to a dose of ionizing radiation between 10 kgy and 50 kgy.

* * * * *

UNITED STATES PATENT AND TRADEMARK OFFICE
CERTIFICATE OF CORRECTION

PATENT NO. : 10,344,253 B2
APPLICATION NO. : 15/519944
DATED : July 9, 2019
INVENTOR(S) : Evan Brutinel Page 1 of 1

It is certified that error appears in the above-identified patent and that said Letters Patent is hereby corrected as shown below:

On the Title Page

Column 2, other publications,
Line 5, delete "laboratomaia" and insert -- laboratornaia --, therefor.

In the Specification

Column 19,
Line 11, delete "Luminar V12" and insert -- Lumar.V12 --, therefor.

Signed and Sealed this
Third Day of September, 2019

Andrei Iancu
*Director of the United States Patent and Trademark Office*